US010429928B2

(12) United States Patent
Morun et al.

(10) Patent No.: US 10,429,928 B2
(45) Date of Patent: *Oct. 1, 2019

(54) SYSTEMS, ARTICLES, AND METHODS FOR CAPACITIVE ELECTROMYOGRAPHY SENSORS

(71) Applicant: CTRL-labs Corporation, New York, NY (US)

(72) Inventors: Cezar Morun, Kitchener (CA); Stephen Lake, Kitchener (CA)

(73) Assignee: CTRL-labs Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/137,960

(22) Filed: Sep. 21, 2018

(65) Prior Publication Data

US 2019/0033967 A1    Jan. 31, 2019

Related U.S. Application Data

(60) Continuation of application No. 15/799,621, filed on Oct. 31, 2017, now Pat. No. 10,101,809, which is a division of application No. 14/539,773, filed on Nov. 12, 2014, now Pat. No. 10,042,422.

(60) Provisional application No. 61/903,238, filed on Nov. 12, 2013.

(51) Int. Cl.
*A61B 5/0492* (2006.01)
*G06F 3/01* (2006.01)
*A61B 5/00* (2006.01)
*G06F 1/16* (2006.01)

(52) U.S. Cl.
CPC ............ *G06F 3/015* (2013.01); *A61B 5/0492* (2013.01); *A61B 5/681* (2013.01); *G06F 1/163* (2013.01); *G06F 3/014* (2013.01); *A61B 2562/247* (2013.01)

(58) Field of Classification Search
CPC .............................. A61B 5/0492; A61B 5/681
USPC .......................................................... 600/393
See application file for complete search history.

*Primary Examiner* — Nadia A Mahmood
(74) *Attorney, Agent, or Firm* — Wolf, Greenfield & Sacks, P.C.

(57) ABSTRACT

Systems, articles, and methods for improved capacitive electromyography ("EMG") sensors are described. The improved capacitive EMG sensors include one or more sensor electrode(s) that is/are coated with a protective barrier formed of a material that has a relative permittivity $\varepsilon_r$ of about 10 or more. The protective barrier shields the sensor electrode(s) from moisture, sweat, skin oils, etc. while advantageously contributing to a large capacitance between the sensor electrode(s) and the user's body. In this way, the improved capacitive EMG sensors provide enhanced robustness against variations in skin and/or environmental conditions. Such improved capacitive EMG sensors are particularly well-suited for use in wearable EMG devices that may be worn by a user for an extended period of time and/or under a variety of skin and/or environmental conditions. A wearable EMG device that provides a component of a human-electronics interface and incorporates such improved capacitive EMG sensors is described.

7 Claims, 3 Drawing Sheets

SYSTEMS, ARTICLES, AND METHODS FOR CAPACITIVE ELECTROMYOGRAPHY SENSORS

CROSS-REFERENCE TO RELATED APPLICATIONS

This Application is a Continuation of U.S. application Ser. No. 15/799,621, filed Oct. 31, 2017, entitled "SYSTEMS, ARTICLES, AND METHODS FOR CAPACITIVE ELECTROMYOGRAPHY SENSORS", which is a Division of U.S. application Ser. No. 14/539,773, filed Nov. 12, 2014, entitled "SYSTEMS, ARTICLES, AND METHODS FOR CAPACITIVE ELECTROMYOGRAPHY SENSORS", which is a Non-Provisional of Provisional (35 USC 119(e)) of U.S. application Ser. No. 61/903,238, filed Nov. 12, 2013, entitled "SYSTEMS, ARTICLES, AND METHODS FOR CAPACITIVE ELECTROMYOGRAPHY SENSORS". The entire contents of these applications are incorporated herein by reference in their entirety.

BACKGROUND

Technical Field

The present systems, articles, and methods generally relate to electromyography and particularly relate to capacitive electromyography sensors.

Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that are responsive to (i.e., detect and provide one or more signal(s) in response to detecting) inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to HCIs, but may also be applied to any other form of human-electronics interface.

Electromyography Sensors

Electromyography ("EMG") is a process for detecting and processing the electrical signals generated by muscle activity. EMG devices employ EMG sensors that are responsive to the range of electrical potentials (typically $\mu$V-mV) involved in muscle activity. EMG signals may be used in a wide variety of applications, including: medical monitoring and diagnosis, muscle rehabilitation, exercise and training, prosthetic control, and even in controlling functions of electronic devices.

There are two main types of EMG sensors: intramuscular EMG sensors and surface EMG sensors. As the names suggest, intramuscular EMG sensors are designed to penetrate the skin and measure EMG signals from within the muscle tissue, while surface EMG sensors are designed to rest on an exposed surface of the skin and measure EMG signals from there. Intramuscular EMG sensor measurements can be much more precise than surface EMG sensor measurements; however, intramuscular EMG sensors must be applied by a trained professional, are obviously more invasive, and are less desirable from the patient's point of view. The use of intramuscular EMG sensors is generally limited to clinical settings.

Surface EMG sensors can be applied with ease, are much more comfortable for the patient/user, and are therefore more appropriate for non-clinical settings and uses. For example, human-electronics interfaces that employ EMG, such as those proposed in U.S. Pat. No. 6,244,873 and U.S. Pat. No. 8,170,656, usually employ surface EMG sensors. Surface EMG sensors come in two forms: resistive EMG sensors and capacitive EMG sensors. For both forms of surface EMG sensors, the sensor electrode typically includes a plate of electrically conductive material that is placed against or in very close proximity to the exposed surface of the user's skin. A resistive EMG sensor electrode is typically directly electrically coupled to the user's skin while a capacitive EMG sensor electrode is typically capacitively coupled to the user's skin. In either case, skin and/or environmental conditions, such as hair density, humidity and moisture levels, and so on, can have a significant impact on the performance of the sensor. These parameters are generally controlled for resistive EMG sensors by preparing the user's skin before applying the sensor electrodes. For example, the region of the user's skin where a resistive electrode is to be placed is usually shaved, exfoliated, and slathered with a conductive gel to establish a suitable and stable environment before the resistive electrode is applied. This obviously limits the appeal of resistive EMG sensors to users, in particular for home and/or recreational use. Capacitive EMG sensors are advantageous because they are generally more robust against some skin and environmental conditions, such as hair density, and are typically applied without the elaborate skin preparation measures (e.g., shaving, exfoliating, and applying a conductive gel) that are employed for resistive sensors. However, capacitive EMG sensors are still very sensitive to moisture and performance can degrade considerably when, for example, a user sweats. There is a need in the art for capacitive EMG sensors with improved robustness against variations in skin and/or environmental conditions.

BRIEF SUMMARY

A capacitive electromyography ("EMG") sensor may be summarized as including a substrate; a first sensor electrode carried by the substrate, wherein the first sensor electrode comprises an electrically conductive plate having a first surface that faces the substrate and a second surface that is opposite the first surface; circuitry communicatively coupled to the first sensor electrode; and a dielectric layer formed of a dielectric material that has a relative permittivity of at least about 10, wherein the dielectric layer coats the second surface of the first sensor electrode. The first sensor electrode may be formed of a material including copper. The circuitry may include at least one circuit selected from the group consisting of: an amplification circuit, a filtering circuit, and an analog-to-digital conversion circuit. At least a portion of the circuitry may be carried by the substrate. The substrate may include a first surface and a second surface, the second surface opposite the first surface across a thickness of the substrate, and the at least a portion of the circuitry may be carried by the first surface of the substrate and the first sensor electrode may be carried by the second surface of the substrate. The dielectric layer may include a ceramic material. The dielectric layer may include an X7R ceramic material. The substrate, the first sensor electrode, and the dielectric layer may constitute a laminate structure. The capacitive EMG sensor may further include an electrically conductive epoxy sandwiched in between the dielectric layer and the first sensor electrode, wherein the dielectric layer is adhered to the first sensor electrode by the electrically conductive epoxy. Alternatively, the capacitive EMG sensor may further include an electrically conductive solder sandwiched in between the dielectric layer and the first sensor electrode, wherein the dielectric layer is adhered to the first sensor electrode by the electrically conductive solder. The dielectric layer may have a thickness of less than about 10 micrometers. The capacitive EMG sensor may be a differential capacitive EMG sensor that further includes a second sensor electrode carried by the substrate, the second sensor electrode comprising an electrically conductive plate having a first surface that faces the substrate and a second surface that is opposite the first surface across a thickness of the second sensor electrode, wherein the second sensor electrode is communicatively coupled to the circuitry, and wherein the dielectric layer coats the second surface of the second sensor electrode. The dielectric layer may comprise a single continuous layer of dielectric material that coats both the second surface of the first sensor electrode and the second surface of the second sensor electrode. The dielectric layer may comprise a first section that coats the second surface of the first sensor electrode and at least a second section that coats the second surface of the second sensor electrode, wherein the first section of the dielectric layer is physically separate from the second section of the dielectric layer. The first sensor electrode and the second sensor electrode may be substantially coplanar. The capacitive EMG sensor may further include a ground electrode carried by the substrate, the ground electrode comprising an electrically conductive plate having a first surface that faces the substrate and a second surface that is opposite the first surface across a thickness of the ground electrode, wherein the ground electrode is communicatively coupled to the circuitry, and wherein the second surface of the ground electrode is exposed and not coated by the dielectric layer. The capacitive EMG sensor may further include at least one additional layer that is sandwiched in between the first sensor electrode and the substrate.

A method of fabricating a capacitive EMG sensor may be summarized as including forming at least a portion of at least one circuit on a first surface of a substrate; forming a first sensor electrode on a second surface of the substrate, the second surface of the substrate opposite the first surface of the substrate across a thickness of the substrate, wherein the first sensor electrode comprises an electrically conductive plate; forming at least one electrically conductive pathway that communicatively couples the first sensor electrode and the at least a portion of at least one circuit; and coating the first sensor electrode with a dielectric layer comprising a dielectric material that has a relative permittivity of at least about 10. Coating the first sensor electrode with a dielectric layer may include coating at least a portion of the second surface of the substrate with the dielectric layer. Coating the first sensor electrode with a dielectric layer may include coating the first sensor electrode with a ceramic material. Coating the first sensor electrode with a dielectric layer may include coating the first sensor electrode with an X7R ceramic material. The capacitive EMG sensor may be a differential capacitive EMG sensor and the method may further include forming a second sensor electrode on the second surface of the substrate, wherein the second sensor electrode comprises an electrically conductive plate; forming at least one electrically conductive pathway that communicatively couples the second sensor electrode and the at least a portion of at least one circuit; and coating the second sensor electrode with the dielectric layer. The method may further include forming a ground electrode on the second surface of the substrate, wherein the ground electrode comprises an electrically conductive plate; and forming at least one electrically conductive pathway that communicatively couples the ground electrode and the at least a portion of at least one circuit. Coating the first sensor electrode with a dielectric layer may include selectively coating the first sensor electrode with the dielectric layer and not coating the ground electrode with the dielectric layer. Coating the first sensor electrode with a dielectric layer may include coating both the first sensor electrode and the ground electrode with the dielectric layer, and the method may further include forming a hole in the dielectric layer to expose the ground electrode. Coating the first sensor electrode with a dielectric layer may include depositing a layer of electrically conductive epoxy on the first sensor electrode; and depositing the dielectric layer on the layer of electrically conductive epoxy. Coating the first sensor electrode with a dielectric layer may include depositing a layer of electrically conductive solder on the first sensor electrode; and depositing the dielectric layer on the layer of electrically conductive solder.

A wearable EMG device may be summarized as including at least one capacitive EMG sensor responsive to (i.e., to detect and provide one or more signal(s) in response to detecting) muscle activity corresponding to a gesture performed by a user of the wearable EMG device, wherein in response to muscle activity corresponding to a gesture performed by a user of the wearable EMG device, the at least one capacitive EMG sensor provides at least one signal, and wherein the at least one capacitive EMG sensor includes: a first sensor electrode comprising an electrically conductive plate; and a dielectric layer formed of a dielectric material that has a relative permittivity of at least about 10, wherein the dielectric layer coats the first sensor electrode; a processor communicatively coupled to the at least one capacitive EMG sensor to in use process signals provided by the at least one capacitive EMG sensor; and an output terminal communicatively coupled to the processor to transmit signals output by the processor. The dielectric layer may include a ceramic material. The ceramic material may include an X7R ceramic material. The wearable EMG device may further include circuitry that mediates communicative coupling between the at least one capacitive EMG sensor and the processor, wherein the circuitry includes at least one circuit selected from the group consisting of: an amplification circuit, a filtering circuit, and an analog-to-digital conversion circuit. The dielectric layer of the at least one capacitive EMG sensor may have a thickness of less than about 10 micrometers. The at least one capacitive EMG sensor may include at least one differential capacitive EMG sensor, and the at least one differential capacitive EMG sensor may further include a second sensor electrode comprising an electrically conductive plate, wherein the dielectric layer coats the second sensor electrode. The at least one capacitive EMG sensor may further include a ground electrode comprising an electrically conductive plate, wherein the ground electrode is exposed and not coated by the dielectric layer.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electric circuits, and in particular printed circuit boards, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for capacitive EMG sensors with improved robustness against variations in skin and/or environmental conditions. In particular, the present systems, articles, and methods describe capacitive EMG sensor designs that employ at least one capacitive electrode having a protective coating that provides a barrier to moisture and a high relative permittivity $\varepsilon_r$. These capacitive EMG sensor designs may be used in any device or method involving capacitive EMG sensing, though they are particularly well-suited for use in applications involving long-term coupling to a user's body over a range of evolving skin and/or environmental conditions. An example application in a wearable EMG device that forms part of a human-electronics interface is described.

Throughout this specification and the appended claims, the terms "coating" and "coat," and variants thereof, are used both as nouns and as verbs to indicate a relationship (noun) or the formation of a relationship (verb) in which a layer of material overlies, underlies, or generally "covers" at least a portion of a device or component, either directly or through one or more intervening layers.

Figure 1:
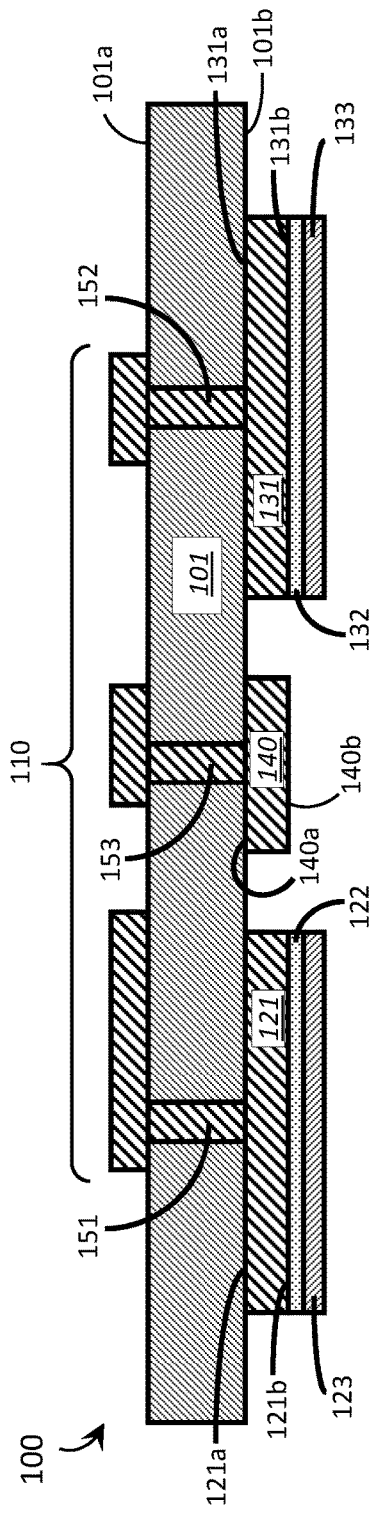
FIG. 1 is a cross-sectional view of an improved capacitive EMG sensor that provides enhanced robustness against variations in skin and/or environmental conditions in accordance with the present systems, articles, and methods.

FIG. 1 is a cross-sectional view of an example of an improved capacitive EMG sensor 100 that provides enhanced robustness against variations in skin and/or environmental conditions in accordance with the present systems, articles, and methods. Exemplary sensor 100 is a differential capacitive EMG sensor that includes two capacitive sensor electrodes 121 and 131, though the teachings described herein are also applicable to single-ended sensor systems that employ only a single capacitive sensor electrode (i.e., one of sensor electrodes 121 or 131). Differential sensor 100 comprises a substrate 101 having a first surface 101a and a second surface 101b opposite the first surface 101a across a thickness of substrate 101. First surface 101a carries at least a portion of at least one circuit (generally, circuitry 110) and second surface 101b carries first sensor electrode 121, second sensor electrode 131, and a ground electrode 140. As will be described in more detail later, circuitry 110 may include at least a portion of at least one electrical or electronic circuit to process signals provided by first and second sensor electrodes 121, 131, including, for example, at least a portion of at least one amplification circuit, at least a portion of at least one filtering circuit, and/or at least a portion of at least one analog-to-digital conversion circuit.

First sensor electrode 121 includes an electrically conductive plate formed of an electrically conductive material (such as, for example, copper or a material including copper) and has a first surface 121a and a second surface 121b, second surface 121b being opposite first surface 121a across a thickness of electrode 121. First sensor electrode 121 is carried by second surface 101b of substrate 101 such that first surface 121a of first sensor electrode 121 faces second surface 101b of substrate 101. Throughout this specification and the appended claims, the terms "carries" and "carried by" are generally used to describe a spatial relationship in which a first layer/component is positioned proximate and physically coupled to a surface of a second layer/component, either directly or through one or more intervening layers/components. For example, circuitry 110 is carried by first surface 101a of substrate 101 and first sensor electrode 121 is carried by second surface 101b of substrate 101. Circuitry 110 is directly carried by first surface 101a of substrate 101 because there are no intervening layers/components that mediate the physical coupling between circuitry 110 and first surface 101a of substrate 101; however, circuitry 110 would still be considered "carried by" first surface 101a of substrate 101 even if the physical coupling between circuitry 110 and first surface 101a of substrate 101 was mediated by at least one intervening layer/component. The terms "carries" and "carried by" are not intended to denote a particular orientation with respect to top and bottom and/or left and right.

First sensor electrode 121 is communicatively coupled to circuitry 110 by at least one electrically conductive pathway 151, which in the illustrated example of FIG. 1 is realized by a via connection that extends through substrate 101.

In accordance with the present systems, articles, and methods, first sensor electrode 121 is coated by a dielectric layer 123 formed of a material that has a relative permittivity $\varepsilon_r$ of at least 10, and by an adhesive layer 122 that is sandwiched in between first sensor electrode 121 and dielectric layer 123. Adhesive layer 122 serves to adhere, affix, or otherwise couple dielectric layer 123 to the second surface 121b of first sensor electrode 121, and may comprise, for example, an electrically conductive epoxy or an electrically conductive solder. In other words, adhesive layer 122 mediates physical and electrical coupling between dielectric layer 123 and first sensor electrode 121. Referring back to the definition of the terms "carries" and "carried by," both adhesive layer 122 and dielectric layer 123 are considered to be carried by second surface 101b of substrate 101.

Dielectric layer 123 may comprise any dielectric material that has a large relative permittivity $\varepsilon_r$ (e.g., a relative permittivity of about 10 or more, including a relative permittivity of about 10, about 20, about 50, about 100, about 1000, etc.). Advantageously, dielectric layer 123 may comprise a ceramic material, such as an X7R ceramic material. Throughout this specification and the appended claims, the term "X7R" refers to the EIA RS-198 standard three-digit code for temperature ranges and inherent change of capacitance. Specifically, the code "X7R" indicates a material that will operate in the temperature range of −55° C. to +125° C. with a change of capacitance of ±15%. A person of skill in the art will appreciate that the X7R EIA code is substantially equivalent to "2X1" under the IEC/EN 60384-9/22 standard. Dielectric layer 123 may comprise a resin and/or ceramic powder such as those used in FaradFlex® products available from Oak-Mitsui Technologies.

Since capacitive EMG sensor 100 is differential, it includes a second sensor electrode 131. Second sensor electrode 131 may be substantially similar to first sensor electrode 121 in that second sensor electrode 131 includes an electrically conductive plate formed of an electrically conductive material (e.g., a material including copper) that has a first surface 131a and a second surface 131b, second surface 131b being opposite first surface 131a across a thickness of electrode 131. Second sensor electrode 131 is carried by second surface 101b of substrate 101 such that first surface 131a of second sensor electrode 131 faces second surface 101b of substrate 101. Second sensor electrode 131 is also coated by a dielectric layer 133 that is substantially similar to dielectric layer 123, and dielectric layer 133 is adhered, affixed, or otherwise coupled to second surface 131b of second sensor electrode 131 by an adhesive layer 132 that is substantially similar to adhesive layer 122. Second sensor electrode 131 is communicatively coupled to circuitry 110 by at least one electrically conductive pathway 152, which in the illustrated example of FIG. 1 is realized by a via connection that extends through substrate 101. As is the case for the illustrated example of FIG. 1, first sensor electrode 121 and second sensor electrode 131 may be substantially coplanar.

Capacitive EMG sensor 100 also includes a ground electrode 140. Ground electrode 140 includes an electrically conductive plate formed of an electrically conductive material (e.g., the same material that makes up first sensor electrode 121 and second sensor electrode 131) that has a first surface 141a and a second surface 141b, second surface 141b being opposite first surface 141a across a thickness of electrode 140. Ground electrode 140 is carried by second surface 101b of substrate 101 such that first surface 140a of ground electrode 140 faces second surface 101b of substrate 101. Ground electrode 140 is communicatively coupled to circuitry 110 by at least one electrically conductive pathway 153, which in the illustrated example of FIG. 1 is realized by a via connection that extends through substrate 101. Unlike second surface 121b of first sensor electrode 121 and second surface 131b of second sensor electrode 131, second surface 140b of ground electrode 140 is exposed and not coated by a dielectric layer in order that ground electrode 140 may advantageously provide a directly electrically coupled (i.e., resistively coupled) path to ground.

In use, capacitive EMG sensor 100 is positioned proximate a user's muscle(s) so that dielectric layers 123, 133 and ground electrode 140 are all in physical contact with the user's skin (or, in some cases, a layer of material such as clothing may mediate physical contact between sensor 100 and the user's skin). Dielectric layers 123, 133 are advantageously formed of a dielectric material that has a high relative permittivity (e.g., $\varepsilon_r$ greater than or equal to about 10) in order to enhance the capacitive coupling between sensor electrodes 121, 131 and the user's body. For each of first sensor electrode 121 and second sensor electrode 131, the respective capacitance that couples the sensor electrode (121, 131) to the user's body (e.g., skin) is at least approximately given by equation 1:

$$C = \frac{\varepsilon_r \varepsilon_0 A}{d} \quad (1)$$

where $\varepsilon_r$ is the relative permittivity of the dielectric material that coats the sensor electrode (i.e., dielectric layers 123, 133), $\varepsilon_o$ is the vacuum permittivity (i.e., a constant value of $8.8541878176\times10^{-12}$ F/m), A is the area of the sensor electrode, and d is the distance between the sensor electrode and the user's body. Thus, if A and d are held constant, $\varepsilon_r$ (i.e., the relative permittivity of dielectric layers 123, 133) directly influences the capacitance between the user's body and each of first sensor electrode 121 and second sensor electrode 131. A large $\varepsilon_r$ may enable a capacitive EMG sensor to employ smaller sensor electrode area(s) A and/or greater separation d between the sensor electrode(s) and the user's body.

Dielectric layers 123, 133 are advantageously bio-compatible (e.g., non-toxic, etc.) and substantially robust against the corrosive effects of sweat and skin oils. Dielectric layers 123, 133 are also advantageously non-absorptive and impermeable to water, sweat, and skin oils. Ideally, dielectric layers 123, 133 provide hermetic barriers between the user's skin and first and second sensor electrodes 121, 131 such that the presence of sweat, water, and/or skin oils does not substantially degrade the performance of capacitive EMG sensor 100.

Even though dielectric layers 123, 133 may protect first sensor electrode 121 and second sensor electrode 131 (respectively) from moisture and/or other aspects of the user's skin, such moisture and/or other aspects that may underlie dielectric layers 123, 133 (e.g., sweat or skin oils that may mediate coupling between the user's body and dielectric layers 123, 133) may still affect the capacitive coupling between the user's body and first and second sensor electrodes 121, 131. This is a further reason why it is advantageous for dielectric layers 123, 133 to be formed of a dielectric material that has a high relative permittivity (i.e., $\varepsilon_r \geq 10$): the larger the relative permittivity of dielectric layers 123, 133, the larger the capacitance that couples the user's body to first and second sensor electrodes 121, 131 and the smaller the proportionate impact of variations in sweat or skin oil conditions.

Equation 1 shows that the capacitance C that couples the user's body to first and second sensor electrodes 121, 131 is directly proportional to the relative permittivity $\varepsilon_r$ and inversely proportional to the thickness d of dielectric layers 123, 133. Thus, while it is advantageous for dielectric layers 123, 133 to be formed of a dielectric material that has a high relative permittivity $\varepsilon_r$, it is similarly advantageous for dielectric layers 123, 133 to be relatively thin (i.e., for d to be small). In accordance with the present systems, articles, and methods, the thickness of dielectric layers 123, 133 may be, for example, approximately 10 µm or less. Approximately 10 µm or less is sufficiently thick to provide an adequate barrier to moisture (e.g., sweat/oil) and electrical insulation, and sufficiently thin to provide an adequate capacitance C as per equation 1.

In accordance with the present systems, articles, and methods, ground electrode 140 is exposed and not coated by a dielectric layer. This is because it is advantageous for ground electrode 140 to be resistively coupled to the user's body as opposed to capacitively coupled thereto in order to provide a lower impedance for return currents.

Even though first and second sensor electrodes 121, 131 are coated by dielectric layers 123, 133 (respectively) and ground electrode 140 is not coated by a dielectric layer, dielectric layers 123, 133 and ground electrode 140 may all still simultaneously contact a user's skin when capacitive EMG sensor 100 is positioned on the user. This is because the surface of the user's skin may have a curvature and/or the surface of the user's skin (and/or the flesh thereunder) may be elastic and compressible such that dielectric layers 123, 133 can be "pressed" into the user's skin with sufficient depth to enable physical contact between ground electrode 140 and the user's skin. While not drawn to scale, in the illustrated example of FIG. 1, dielectric layers 123, 133 are still thinner than the electrically conductive plates that form first and second sensor electrodes 121, 131. For example, dielectric layers 123, 133 may each have a thickness of less than about 10 µm while first and second sensor electrodes 121, 131 may each have a thickness of about 30 µm or more.

There are many different ways in which dielectric layers 123, 133 may be applied to coat first and second sensor electrodes 121, 131 (respectively) and the specific structural configuration of the corresponding capacitive EMG sensor may vary to reflect this. In exemplary capacitive EMG sensor 100, dielectric layers 123, 133 have been individually and separately deposited on first and second sensor electrodes 121, 131 (respectively). This may be achieved by, for example, brushing a liquid or fluid form of the dielectric material that constitutes dielectric layers 123 and 133 over second surface 121*b* of first sensor electrode 121 and second surface 131*b* of second sensor electrode 131. In this case, dielectric layers 123, 133 may subsequently be hardened or cured (and adhesive layers 122, 132 may potentially not be required). Alternatively, individual and separate sections of a substantially solid or non-fluid form of the dielectric material that constitutes dielectric layers 123 and 133 may be sized and dimensioned to at least approximately match the respective areas of first and second sensor electrodes 121, 131 and then respective ones of such sections may be deposited on first and second sensor electrodes 121 and 131. For example, a first section of a dielectric material (having a high relative permittivity) may be sized and dimensioned to at least approximately match the area of first sensor electrode 121 and this first section of the dielectric material may be adhered, affixed, or otherwise coupled to first sensor electrode 121 by adhesive layer 122 to form dielectric layer 123. Likewise, a second section of the dielectric material may be sized and dimensioned to at least approximately match the area of second sensor electrode 131 and adhered, affixed, or otherwise coupled to second sensor electrode 131 by adhesive layer 132 to form dielectric layer 133.

As an alternative to the above examples of depositing dielectric layers 121, 131 as individual, separate sections of dielectric material, a single continuous piece of dielectric material may be deposited over second surface 101*b* of substrate 101, first and second sensor electrodes 121, 131, and optionally ground electrode 140. In this case, substrate 101, first and second sensors electrodes 121, 131, and dielectric layers 123, 133 may together constitute a laminate structure. In other words, dielectric layers 123, 133 may be applied to first and second sensor electrodes 121, 131 as lamination layers using a lamination process. In fabrication processes in which dielectric material coats ground electrode 140, the portion of dielectric material that coats ground electrode may subsequently be removed (e.g., by an etching process) to expose second surface 140*b* of ground electrode 140.

Figure 2:
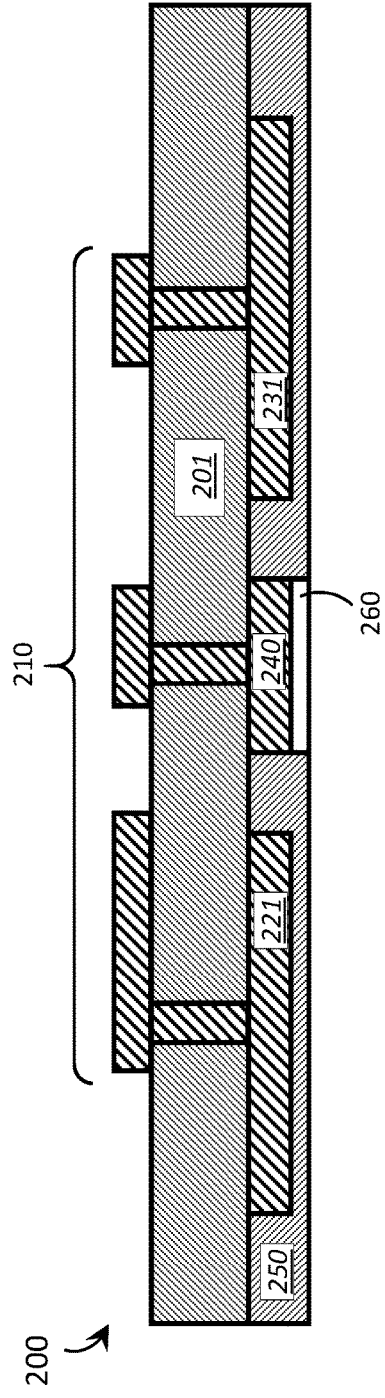
FIG. 2 is a cross-sectional view of a laminate version of an improved capacitive EMG sensor that provides enhanced robustness against variations in skin and/or environmental conditions in accordance with the present systems, articles, and methods.

FIG. 2 is a cross-sectional view of an exemplary laminate version of an improved capacitive EMG sensor 200 that provides enhanced robustness against variations in skin and/or environmental conditions in accordance with the present systems, articles, and methods. Exemplary sensor 200 is a differential capacitive EMG sensor that is substantially similar to sensor 100 from FIG. 1 in that sensor 200 includes a substrate 201 (substantially similar to substrate 101 from sensor 100), circuitry 210 (substantially similar to circuitry 110 from sensor 100), first and second capacitive sensor electrodes 221 and 231 (substantially similar to first and second sensor electrodes 121 and 131, respectively, from sensor 100), and ground electrode 240 (substantially similar to ground electrode 140 from sensor 100). Sensor 200 also includes a dielectric layer 250 that coats first and second sensor electrodes 221, 231 in a similar way to dielectric layers 123, 133 from sensor 100. Like dielectric layers 123 and 133, dielectric layer 250 is formed of a dielectric material that has a large relative permittivity (i.e., $\varepsilon_r$ greater than or equal to about 10). However, unlike dielectric layers 123 and 133, dielectric layer 250 is deposited as a single continuous layer that coats both first and second sensor electrodes 221, 231 and also coats at least a portion of substrate 201. For example, sensor 200 may be a laminate structure and dielectric layer 250 may be deposited using a lamination process. The deposition of dielectric layer 250 may initially coat ground electrode 240, in which case ground electrode 240 may subsequently be exposed by forming (e.g., etching) a hole 260 in dielectric layer 250. Otherwise, a temporary mask may cover ground electrode 240 during deposition of dielectric layer 250 to prevent dielectric layer 250 from coating ground electrode 240 and hole 260 may be left as a result when the mask is subsequently removed.

Dielectric layer 250 may be deposited to provide a desired thickness of, for example, less than about 10 µm measured from the interface with first and second sensor electrodes 221, 231. Though not illustrated in FIG. 2, an adhesive layer may be used to adhere, affix, or otherwise couple dielectric layer 250 to any or all of substrate 201, first electrode 221, and/or second sensor electrode 231.

Various methods for fabricating an improved capacitive EMG sensor that includes at least one protective, high-$\varepsilon_r$ dielectric barrier have been described. These methods are summarized and generalized in FIG. 3.

Figure 3:
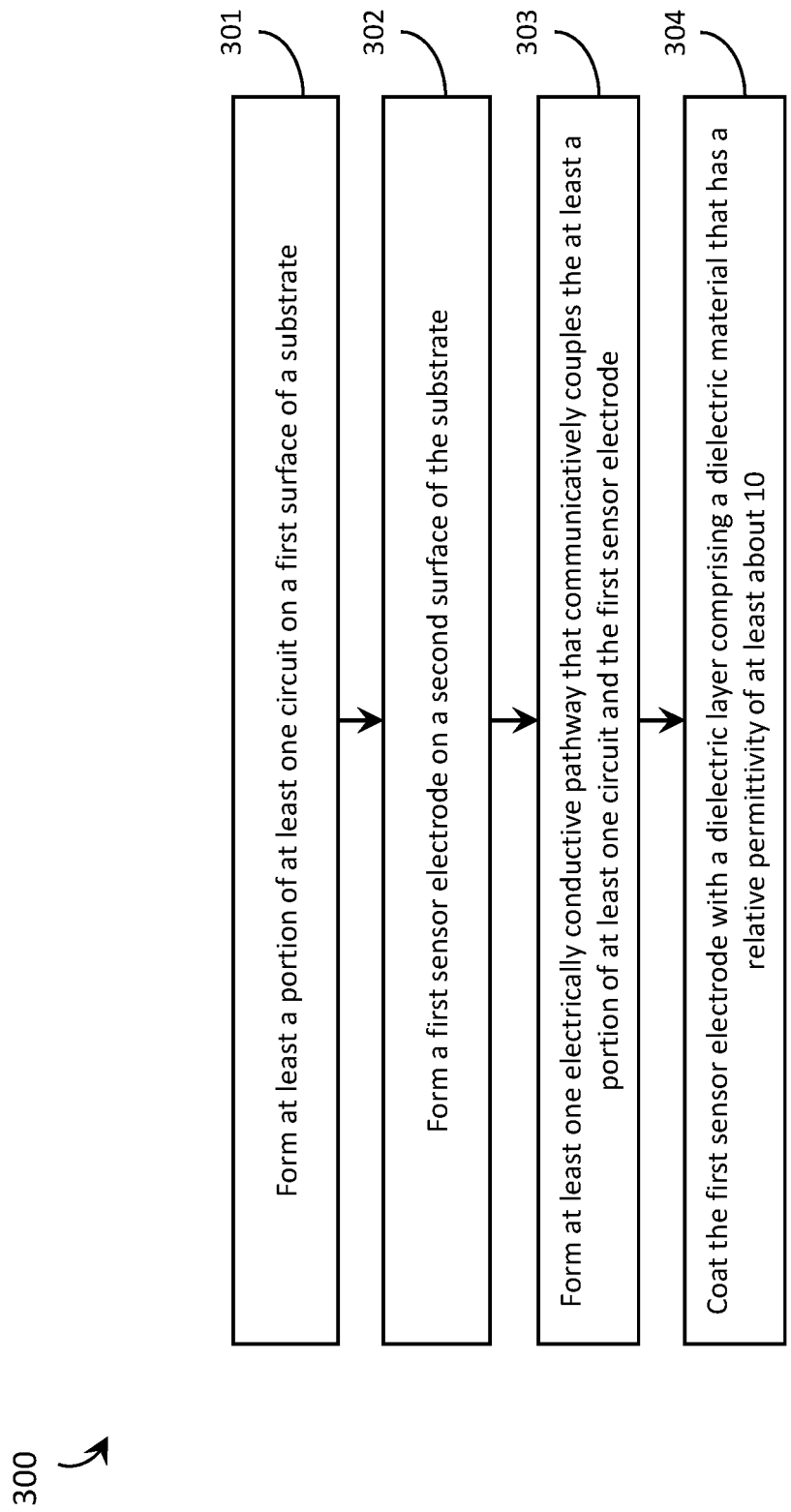
FIG. 3 is a flow-diagram showing a method of fabricating an improved capacitive EMG sensor in accordance with the present systems, articles, and methods.

FIG. 3 is a flow-diagram showing a method 300 of fabricating an improved capacitive EMG sensor (e.g., sensor 100 and/or sensor 200) in accordance with the present systems, articles, and methods. Method 300 includes four acts 301, 302, 303, and 304, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments.

At 301, at least a portion of at least one circuit is formed on a first surface of a substrate. The at least a portion of at least one circuit may include one or more conductive traces and/or one or more electrical or electronic circuits, such as one or more amplification circuit(s), one or more filtering circuit(s), and/or one or more analog-to-digital conversion circuit(s). As examples, sensor 100 from FIG. 1 includes circuitry 110 and sensor 200 from FIG. 2 includes circuitry 210. Forming at least a portion of at least one circuit may include one or more lithography process(es) and/or soldering one or more component(s) to the substrate.

At 302, a first sensor electrode is formed on a second surface of the substrate. The first sensor electrode may include an electrically conductive plate formed of, for example, a material including copper. As examples, sensor 100 from FIG. 1 includes first sensor electrode 121 and sensor 200 from FIG. 2 includes first sensor electrode 221. Forming the first sensor electrode may include, for example, one or more lithography process(es). As previously described, the order of the acts of method 300 may change. For example, in some cases it may be advantageous to form the first sensor electrode per act 302 prior to forming the at least a portion of circuitry per act 301.

At 303, at least one electrically conductive pathway that communicatively couples the at least a portion of at least one circuit and the first sensor electrode is formed. The at least one electrically conductive pathway may include at least one via through the substrate, at least one conductive trace, and/or at least one wiring component. For example, sensor 100 includes electrically conductive pathway 151 that communicatively couples circuitry 110 to first sensor electrode 121. In some implementations, all or a portion of a via (e.g., a hole or aperture with or without electrically conductive communicative path therethrough) may be formed in the substrate before either or both of acts 301 and/or 302.

At 304, the first sensor electrode is coated with a dielectric layer comprising a dielectric material that has a relative permittivity $\varepsilon_r$ of at least 10. As previously described, the coating may be applied in a variety of different ways, including without limitation: brushing or otherwise applying a fluid form of the dielectric material on the first sensor electrode and curing the dielectric material; adhering, affixing, or otherwise coupling a substantially non-fluid form of the dielectric material to the first sensor electrode using, for example, an adhesive layer such as an electrically conductive epoxy or an electrically conductive solder; or depositing a single continuous layer of the dielectric material over both the first sensor electrode and at least a portion of the substrate using a lamination process or other dielectric deposition process. When an adhesive layer is used, coating the first sensor electrode with a dielectric layer may include depositing a layer of electrically conductive epoxy on the first sensor electrode and depositing the dielectric layer on the layer of electrically conductive epoxy, or depositing a layer of electrically conductive solder on the first sensor electrode and depositing the dielectric layer on the layer of electrically conductive solder. As examples, sensor 100 includes dielectric layer 123 that is adhered to first sensor electrode 121 by adhesive layer 122 and sensor 200 includes dielectric layer 250 that is deposited over first sensor electrode 221 and substrate 201 to form a laminate structure. The dielectric layer may include a ceramic material, such as an X7R ceramic material.

In addition to acts 301, 302, 303, and 304, method 300 may be extended to include further acts in order to, for example, fabricate some of the additional elements and/or features described for sensors 100 and 200. For example, method 300 may include forming a second sensor electrode on the second surface of the substrate, forming at least one electrically conductive pathway that communicatively couples the at least a portion of at least one circuit and the second sensor electrode, and coating the second sensor electrode with the dielectric layer (either with a single continuous dielectric layer or with a separate section of the dielectric layer, as described previously). Either separately or in addition to forming a second sensor electrode, method 300 may include forming a ground electrode on the second surface of the substrate and forming at least one electrically conductive pathway that communicatively couples the ground electrode and the at least a portion of at least one circuit. In this case, coating the first sensor electrode with a dielectric layer per act 303 may include selectively coating the first sensor electrode with the dielectric layer and not coating the ground electrode with the dielectric layer, or coating both the first sensor electrode and the ground electrode with the dielectric layer and then forming a hole in the dielectric layer to expose the ground electrode.

The improved capacitive EMG sensors described herein may be implemented in virtually any system, device, or process that makes use of capacitive EMG sensors; however, the improved capacitive EMG sensors described herein are particularly well-suited for use in EMG devices that are intended to be worn by (or otherwise coupled to) a user for an extended period of time and/or for a range of different skin and/or environmental conditions. As an example, the improved capacitive EMG sensors described herein may be implemented in a wearable EMG device that provides gesture-based control in a human-electronics interface. Some details of exemplary wearable EMG devices that may be adapted to include at least one improved capacitive EMG sensor from the present systems, articles, and methods are described in, for example, U.S. Provisional Patent Application Ser. No. 61/903,238; U.S. Provisional Patent Application Ser. No. 61/768,322 (now U.S. Non-Provisional patent application Ser. No. 14/186,889); Provisional Patent Application Ser. No. 61/771,500 (now U.S. Non-Provisional patent application Ser. No. 14/194,252); Provisional Patent Application Ser. No. 61/857,105 (now U.S. Non-Provisional patent application Ser. No. 14/335,668); Provisional Patent Application Ser. No. 61/860,063 (now U.S. Non-Provisional patent application Ser. No. 14/276,575); Provisional Patent Application Ser. No. 61/866,960 (now U.S. Non-Provisional patent application Ser. No. 14/461,044); Provisional Patent Application Ser. No. 61/869,526 (now U.S. Non-Provisional patent application Ser. No. 14/465,194); Provisional Patent Application Ser. No. 61/881,064 (now U.S. Non-Provisional patent application Ser. No. 14/494,274); and Provisional Patent Application Ser. No. 61/894,263 (now U.S. Non-Provisional patent application Ser. No. 14/520,081), all of which are incorporated herein by reference in their entirety.

Throughout this specification and the appended claims, the term "gesture" is used to generally refer to a physical action (e.g., a movement, a stretch, a flex, a pose, etc.) performed or otherwise effected by a user. Any physical action performed or otherwise effected by a user that involves detectable muscle activity (detectable, e.g., by at least one appropriately positioned EMG sensor) may constitute a gesture in the present systems, articles, and methods.

Figure 4:
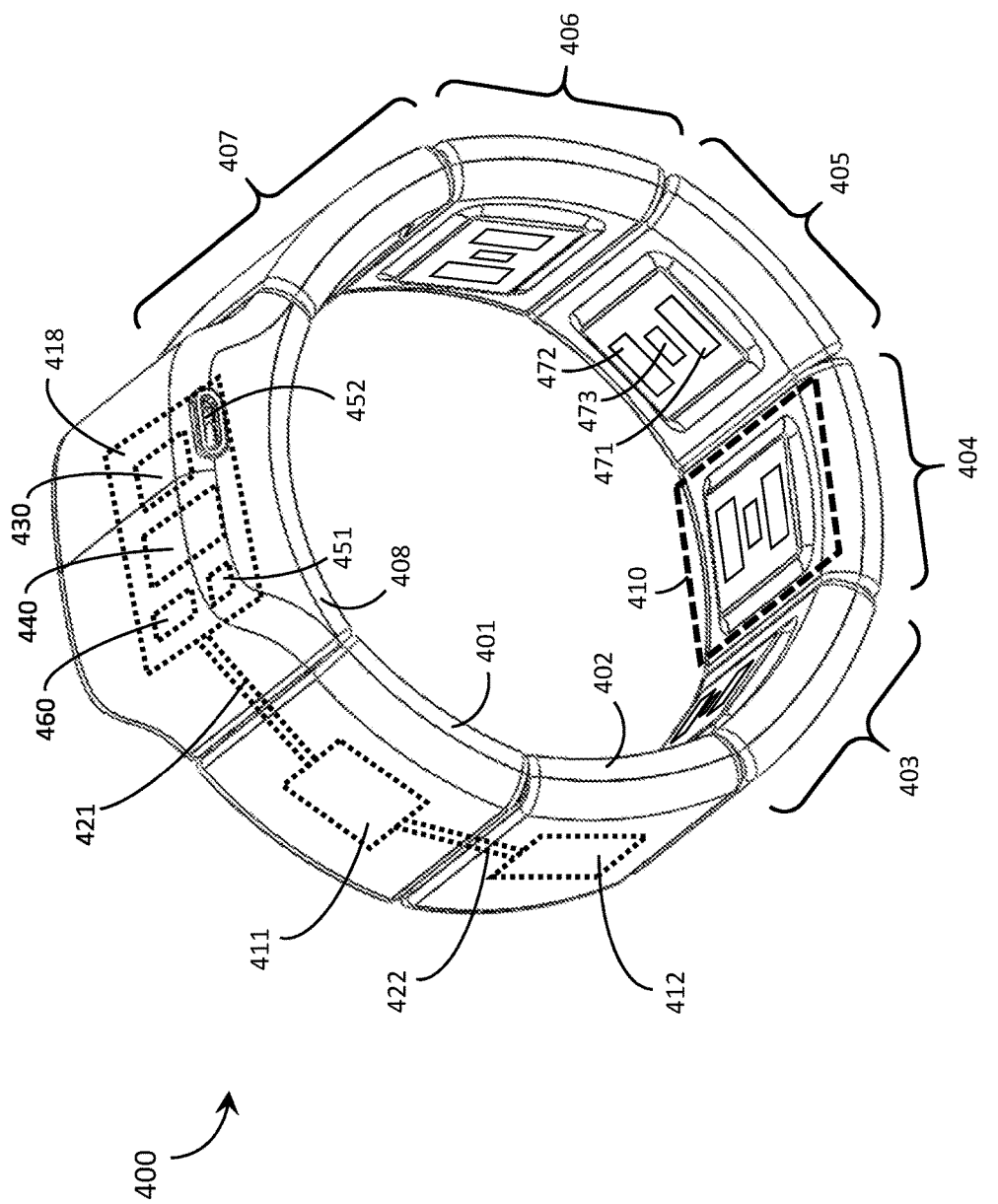
FIG. 4 is a perspective view of an exemplary wearable EMG device that includes improved capacitive EMG sensors in accordance with the present systems, articles, and methods.

FIG. 4 is a perspective view of an exemplary wearable EMG device 400 that includes improved capacitive EMG sensors in accordance with the present systems, articles, and methods. Exemplary wearable EMG device 400 may, for example, form part of a human-electronics interface. Exemplary wearable EMG device 400 is an armband designed to be worn on the forearm of a user, though a person of skill in the art will appreciate that the teachings described herein may readily be applied in wearable EMG devices designed to be worn elsewhere on the body of the user, including without limitation: on the upper arm, wrist, hand, finger, leg, foot, torso, or neck of the user.

Device 400 includes a set of eight pod structures 401, 402, 403, 404, 405, 406, 407, and 408 that form physically coupled links of the wearable EMG device 400. Each pod structure in the set of eight pod structures 401, 402, 403, 404, 405, 406, 407, and 408 is positioned adjacent and in between two other pod structures in the set of eight pod structures such that the set of pod structures forms a perimeter of an annular or closed loop configuration. For example, pod structure 401 is positioned adjacent and in between pod structures 402 and 408 at least approximately on a perimeter of the annular or closed loop configuration of pod structures, pod structure 402 is positioned adjacent and in between pod structures 401 and 403 at least approximately on the perimeter of the annular or closed loop configuration, pod structure 403 is positioned adjacent and in between pod structures 402 and 404 at least approximately on the perimeter of the annular or closed loop configuration, and so on. Each of pod structures 401, 402, 403, 404, 405, 406, 407, and 408 is physically coupled to the two adjacent pod structures by at least one adaptive coupler (not visible in FIG. 4). For example, pod structure 401 is physically coupled to pod structure 408 by an adaptive coupler and to pod structure 402 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 401, 402, 403, 404, 405, 406, 407, and 408 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 400 is depicted in FIG. 4 with the at least one adaptive coupler completely retracted and contained within the eight pod structures 401, 402, 403, 404, 405, 406, 407, and 408 (and therefore the at least one adaptive coupler is not visible in FIG. 4).

Throughout this specification and the appended claims, the term "pod structure" is used to refer to an individual link, segment, pod, section, structure, component, etc. of a wearable EMG device. For the purposes of the present systems, articles, and methods, an "individual link, segment, pod, section, structure, component, etc." (i.e., a "pod structure") of a wearable EMG device is characterized by its ability to be moved or displaced relative to another link, segment, pod, section, structure component, etc. of the wearable EMG device. For example, pod structures 401 and 402 of device 400 can each be moved or displaced relative to one another within the constraints imposed by the adaptive coupler providing adaptive physical coupling therebetween. The desire for pod structures 401 and 402 to be movable/displaceable relative to one another specifically arises because device 400 is a wearable EMG device that advantageously accommodates the movements of a user and/or different user forms.

Device 400 includes eight pod structures 401, 402, 403, 404, 405, 406, 407, and 408 that form physically coupled links thereof. Wearable EMG devices employing pod structures (e.g., device 400) are used herein as exemplary wearable EMG device designs, while the present systems, articles, and methods may be applied to wearable EMG devices that do not employ pod structures (or that employ any number of pod structures). Thus, throughout this specification, descriptions relating to pod structures (e.g., functions and/or components of pod structures) should be interpreted as being applicable to any wearable EMG device design, even wearable EMG device designs that do not employ pod structures (except in cases where a pod structure is specifically recited in a claim).

In exemplary device 400 of FIG. 4, each of pod structures 401, 402, 403, 404, 405, 406, 407, and 408 comprises a respective housing having a respective inner volume. Each housing may be formed of substantially rigid material and may be optically opaque. Throughout this specification and the appended claims, the term "rigid" as in, for example, "substantially rigid material," is used to describe a material that has an inherent tendency to maintain or restore its shape and resist malformation/deformation under the moderate stresses and strains typically encountered by a wearable electronic device.

Details of the components contained within the housings (i.e., within the inner volumes of the housings) of pod structures 401, 402, 403, 404, 405, 406, 407, and 408 are not necessarily visible in FIG. 4. To facilitate descriptions of exemplary device 400, some internal components are depicted by dashed lines in FIG. 4 to indicate that these components are contained in the inner volume(s) of housings and may not normally be actually visible in the view depicted in FIG. 4, unless a transparent or translucent material is employed to form the housings. For example, any or all of pod structures 401, 402, 403, 404, 405, 406, 407, and/or 408 may include circuitry (i.e., electrical and/or electronic circuitry). In FIG. 4, a first pod structure 401 is shown containing circuitry 411 (i.e., circuitry 411 is contained in the inner volume of the housing of pod structure 401), a second pod structure 402 is shown containing circuitry 412, and a third pod structure 408 is shown containing circuitry 418. The circuitry in any or all pod structures may be communicatively coupled to the circuitry in at least one other pod structure by at least one communicative pathway (e.g., by at least one electrically conductive pathway and/or by at least one optical pathway). For example, FIG. 4 shows a first set of communicative pathways 421 providing communicative coupling between circuitry 418 of pod structure 408 and circuitry 411 of pod structure 401, and a second set of communicative pathways 422 providing communicative coupling between circuitry 411 of pod structure 401 and circuitry 412 of pod structure 402.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings, magnetic couplings, and/or optical couplings.

Each individual pod structure within a wearable EMG device may perform a particular function, or particular functions. For example, in device 400, each of pod structures 401, 402, 403, 404, 405, 406, and 407 includes a respective improved capacitive EMG sensor 410 (only one called out in FIG. 4 to reduce clutter) in accordance with the present systems, articles, and methods. Each improved capacitive EMG sensor 410 is responsive to muscle activity corresponding to a gesture performed by a user of wearable EMG device 400. Thus, each improved capacitive EMG sensor 410 is included in device 400 to detect muscle activity of a user and to provide electrical signals in response to the detected muscle activity. Thus, each of pod structures 401, 402, 403, 404, 405, 406, and 407 may be referred to as a respective "sensor pod." Throughout this specification and the appended claims, the term "sensor pod" is used to denote an individual pod structure that includes at least one sensor to detect muscle activity of a user.

Pod structure 408 of device 400 includes a processor 430 that processes the signals provided by the improved capacitive EMG sensors 410 of sensor pods 401, 402, 403, 404, 405, 406, and 407 in response to detected muscle activity. Pod structure 408 may therefore be referred to as a "processor pod." Throughout this specification and the appended claims, the term "processor pod" is used to denote an individual pod structure that includes at least one processor to process signals. The processor may be any type of processor, including but not limited to: a digital microprocessor or microcontroller, an application-specific integrated circuit (ASIC), a field-programmable gate array (FPGA), a digital signal processor (DSP), a graphics processing unit (GPU), a programmable gate array (PGA), a programmable logic unit (PLU), or the like, that analyzes or otherwise processes the signals to determine at least one output, action, or function based on the signals. A person of skill in the art will appreciate that implementations that employ a digital processor (e.g., a digital microprocessor or microcontroller, a DSP, etc.) may advantageously include a non-transitory processor-readable storage medium or memory communicatively coupled thereto and storing processor-executable instructions that control the operations thereof, whereas implementations that employ an ASIC, FPGA, or analog processor may or may optionally not include a non-transitory processor-readable storage medium, or may include on-board registers or other non-transitory storage structures.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 400, processor pod 408 includes an improved capacitive EMG sensor 410 (not visible in FIG. 4) responsive to (i.e., to sense, measure, transduce or otherwise detect and provide one or more signal(s) in response to sensing, measuring, transducing, or otherwise detecting) muscle activity of a user, so processor pod 408 could be referred to as a sensor pod. However, in exemplary device 400, processor pod 408 is the only pod structure that includes a processor 430, thus processor pod 408 is the only pod structure in exemplary device 400 that can be referred to as a processor pod. The processor 430 in processor pod 408 also processes the EMG signals provided by the improved capacitive EMG sensor 410 of processor pod 408. In alternative embodiments of device 400, multiple pod structures may include processors, and thus multiple pod structures may serve as processor pods. Similarly, some pod structures may not include sensors, and/or some sensors and/or processors may be laid out in other configurations that do not involve pod structures.

In device 400, processor 430 includes and/or is communicatively coupled to a non-transitory processor-readable storage medium or memory 440. Memory 440 may store processor-executable gesture identification instructions and/or data that, when executed by processor 430, cause processor 430 to process the EMG signals from improved capacitive EMG sensors 410 and identify a gesture to which the EMG signals correspond. For communicating with a separate electronic device (not shown), wearable EMG device 400 includes at least one communication terminal. Throughout this specification and the appended claims, the term "communication terminal" is generally used to refer to any physical structure that provides a telecommunications link through which a data signal may enter and/or leave a device. A communication terminal represents the end (or "terminus") of communicative signal transfer within a device and the beginning of communicative signal transfer to/from an external device (or external devices). As examples, device 400 includes a first communication terminal 451 and a second communication terminal 452. First communication terminal 451 includes a wireless transmitter (i.e., a wireless communication terminal) and second communication terminal 452 includes a tethered connector port 452. Wireless transmitter 451 may include, for example, a Bluetooth® transmitter (or similar) and connector port 452 may include a Universal Serial Bus port, a mini-Universal Serial Bus port, a micro-Universal Serial Bus port, a SMA port, a THUNDERBOLT® port, or the like.

For some applications, device 400 may also include at least one inertial sensor 460 (e.g., an inertial measurement unit, or "IMU," that includes at least one accelerometer and/or at least one gyroscope) responsive to (i.e., to detect, sense, or measure and provide one or more signal(s) in response to detecting, sensing, or measuring) motion effected by a user and provide signals in response to the detected motion. Signals provided by inertial sensor 460 may be combined or otherwise processed in conjunction with signals provided by improved capacitive EMG sensors 410.

As previously described, each of pod structures 401, 402, 403, 404, 405, 406, 407, and 408 may include circuitry (i.e., electrical and/or electronic circuitry). FIG. 4 depicts circuitry 411 inside the inner volume of sensor pod 401, circuitry 412 inside the inner volume of sensor pod 402, and circuitry 418 inside the inner volume of processor pod 418. The circuitry in any or all of pod structures 401, 402, 403, 404, 405, 406, 407 and 408 (including circuitries 411, 412, and 418) may include any or all of: an amplification circuit to amplify electrical signals provided by at least one EMG sensor 410, a filtering circuit to remove unwanted signal frequencies from the signals provided by at least one EMG sensor 410, and/or an analog-to-digital conversion circuit to convert analog signals into digital signals. Device 400 may also include at least one battery (not shown in FIG. 4) to provide a portable power source for device 400.

Each of EMG sensors 410 includes a respective improved capacitive EMG sensor per the present systems, articles, and methods, such as for example sensor 100 from FIG. 1 or sensor 200 from FIG. 2. In particular, each EMG sensor 410 includes a respective first capacitive sensor electrode 471 (only one called out to reduce clutter) that is coated with a dielectric layer formed of a dielectric material having a relative permittivity greater than or equal to about 10, a second capacitive sensor electrode 472 (only one called out to reduce clutter) that is also coated with a dielectric layer formed of a dielectric material having a relative permittivity greater than or equal to about 10, and a ground electrode 473 (only one called out to reduce clutter) that is exposed and not coated by a dielectric layer. Each the electrodes 471, 472, and 473 of each EMG sensor 410 may be carried by a respective substrate, and the respective circuitry (e.g., 411, 412, and 418) of each pod structure 401, 402, 403, 404, 405, 406, 407, and 408 may be carried by the same substrate. For example, each respective EMG sensor 410 of each pod structure 401, 402, 403, 404, 405, 406, 407, and 408 may include a respective substrate, with the circuitry 411, 412, 418 of each pod structure 401, 402, 403, 404, 405, 406, 407, and 408 carried by a first surface of the substrate and the first and second sensor electrodes 471, 472 and the ground electrode 473 carried by a second surface of the substrate, the second surface being opposite the first surface.

The improved capacitive EMG sensors 410 of wearable EMG device 400 are differential sensors that each implement two respective sensor electrodes 471, 472, though the teachings herein may similarly be applied to wearable EMG devices that employ single-ended improved capacitive EMG sensors that each implement a respective single sensor electrode.

Signals that are provided by improved capacitive EMG sensors 410 in device 400 are routed to processor pod 408 for processing by processor 430. To this end, device 400 employs a set of communicative pathways (e.g., 421 and 422) to route the signals that are output by sensor pods 401, 402, 403, 404, 405, 406, and 407 to processor pod 408. Each respective pod structure 401, 402, 403, 404, 405, 406, 407, and 408 in device 400 is communicatively coupled to, over, or through at least one of the two other pod structures between which the respective pod structure is positioned by at least one respective communicative pathway from the set of communicative pathways. Each communicative pathway (e.g., 421 and 422) may be realized in any communicative form, including but not limited to: electrically conductive wires or cables, ribbon cables, fiber-optic cables, optical/photonic waveguides, electrically conductive traces carried by a rigid printed circuit board, electrically conductive traces carried by a flexible printed circuit board, and/or electrically conductive traces carried by a stretchable printed circuit board.

Device 400 from FIG. 4 represents an example of a wearable EMG device that incorporates the teachings of the present systems, articles, and methods, though the teachings of the present systems, articles, and methods may be applicable to any wearable EMG device that includes at least one EMG sensor.

In accordance with the present systems, articles, and methods, a capacitive EMG sensor may be fabricated directly on a substrate that has a high relative permittivity $\varepsilon_r$, such as on a ceramic substrate. For example, referring back to sensor 200 of FIG. 2 using this alternative fabrication approach (which results in re-defining some of the labelled elements of FIG. 2), a capacitive EMG sensor 200 may comprise: a substrate 250 that is formed of a material that has a high relative permittivity (i.e., $\varepsilon_r$ greater than or equal to about 10) such as a ceramic material including but not limited to an X7R ceramic material, at least one sensor electrode 221, 231 deposited on and carried by the substrate 250, a dielectric layer 201 deposited on and carried by the at least one sensor electrode 221, 231 and the substrate 250, circuitry 210 deposited on and carried by the dielectric layer 201, and one or more electrically conductive pathway(s) (e.g., via(s)) that communicatively couple the circuitry 210 to the at least one sensor electrode 221, 231. In this case, the substrate 250 may be thin (e.g., with a thickness of about 10 µm or less) and/or the at least one sensor electrode 221, 231 may be deposited on the substrate 250 by first etching a trench into the substrate 250 (to a depth that leaves a thickness of 10 µm or less of substrate material 250 beneath the trench) and then filling the trench with the sensor electrode material. If the sensor 200 further includes a ground electrode 240, a hole 260 may be etched in the substrate 250 to expose the ground electrode 240.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the processor-readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Non-Provisional patent application Ser. No. 15/799,621; U.S. Non-Provisional patent application Ser. No. 14/539,773; U.S. Provisional Patent Application Ser. No. 61/903,238; U.S. Provisional Patent Application Ser. No. 61/768,322 (now U.S. Non-Provisional patent application Ser. No. 14/186,889); Provisional Patent Application Ser. No. 61/771,500 (now U.S. Non-Provisional patent application Ser. No. 14/194,252); Provisional Patent Application Ser. No. 61/857,105 (now U.S. Non-Provisional patent application Ser. No. 14/335,668); Provisional Patent Application Ser. No. 61/860,063 (now U.S. Non-Provisional patent application Ser. No. 14/276,575); Provisional Patent Application Ser. No. 61/866,960 (now U.S. Non-Provisional patent application Ser. No. 14/461,044); Provisional Patent Application Ser. No. 61/869,526 (now U.S. Non-Provisional patent application Ser. No. 14/465,194); Provisional Patent Application Ser. No. 61/881,064 (now U.S. Non-Provisional patent application Ser. No. 14/494,274); and Provisional Patent Application Ser. No. 61/894,263 (now U.S. Non-Provisional patent application Ser. No. 14/520,081), are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of fabricating an electromyography ("EMG") sensor, the method comprising:
    forming at least a portion of at least one circuit on a first surface of a substrate;
    forming a first electrode on a second surface of the substrate, the second surface of the substrate opposite the first surface of the substrate across a thickness of the substrate, wherein the first electrode comprises a first electrically conductive plate;
    forming at least a first electrically conductive pathway through the substrate that communicatively couples the first electrode and the at least a portion of at least one circuit;
    forming a second electrode on the second surface of the substrate, wherein the second electrode comprises a second electrically conductive plate;
    forming at least a second electrically conductive pathway through the substrate that communicatively couples the second electrode and the at least a portion of at least one circuit.

2. The method of claim 1 wherein forming a first electrode on a second surface of the substrate includes forming a first sensor electrode on the second surface of the substrate.

3. The method of claim 2 wherein forming a second electrode on a second surface of the substrate includes forming a ground electrode on the second surface of the substrate.

4. The method of claim 2 wherein forming a second electrode on a second surface of the substrate includes forming a second sensor electrode on the second surface of the substrate.

5. The method of claim 4, further comprising:
    forming a ground electrode on the second surface of the substrate, wherein the ground electrode comprises a third electrically conductive plate; and
    forming at least a third electrically conductive pathway through the substrate that communicatively couples the ground electrode and the at least a portion of at least one circuit.

6. The method of claim 1 wherein forming a first electrode on a second surface of the substrate and forming a second electrode on the second surface of the substrate include forming the first electrode and the second electrode coplanar to one another on the second surface of the substrate.

7. The method of claim 1 wherein forming at least a portion of at least one circuit on a first surface of a substrate includes forming, on the first surface of the substrate, at least a portion of at least one circuit selected from a group consisting of: an amplification circuit, a filtering circuit, and an analog-to-digital conversion circuit.

* * * * *